(12) United States Patent
Andersen et al.

(10) Patent No.: US 7,777,089 B2
(45) Date of Patent: *Aug. 17, 2010

(54) HYDROCARBON SEPARATION

(75) Inventors: Simon Ivar Andersen, Tikøb (DK); Annette Leerskov, Kastrup (DK); Peter Jakob Mune, Copenhagen (DK)

(73) Assignee: Haldor Topsøe A/S, Lyngby (DK)

( * ) Notice: Subject to any disclaimer, the term of this patent is extended or adjusted under 35 U.S.C. 154(b) by 923 days.

This patent is subject to a terminal disclaimer.

(21) Appl. No.: 11/634,070

(22) Filed: Dec. 6, 2006

(65) Prior Publication Data

US 2008/0139863 A1    Jun. 12, 2008

(51) Int. Cl.
C07C 7/12    (2006.01)
(52) U.S. Cl. ...................... 585/820; 585/825
(58) Field of Classification Search .......... 585/820, 585/825
See application file for complete search history.

(56) References Cited

U.S. PATENT DOCUMENTS

| 2,768,942 | A | | 10/1956 | Marple, Jr. et al. |
| 2,958,714 | A | | 11/1960 | Kearby |
| 4,956,521 | A | | 9/1990 | Volles |
| 5,059,741 | A | * | 10/1991 | Foley ...................... 585/734 |
| 5,565,066 | A | | 10/1996 | Marker et al. |
| 6,069,289 | A | | 5/2000 | Dandekar et al. |
| 6,353,144 | B1 | | 3/2002 | Ragil et al. |
| 7,037,422 | B2 | | 5/2006 | Maesen et al. |
| 2006/0065576 | A1 | | 3/2006 | Broutin et al. |
| 2006/0106266 | A1 | * | 5/2006 | Broutin et al. .............. 585/418 |

FOREIGN PATENT DOCUMENTS

| EP | 0 934 996 A1 | 8/1999 |
| GB | 982445 | 2/1965 |
| WO | WO-94/17017 A1 | 8/1994 |

OTHER PUBLICATIONS

Gounaris et al., "Rational design of shape selective separation and catalysis—I: Concepts and analysis" *Chemical Engineering Science* 61, 2006, pp. 7933-7948.
H. Schulz et al., "Deactivation of HZSM5 Zeolite During Methanol Conversion: Kinetic Probing of Pore-Architecture and Acidic Properties", Catalyst Deactivation 1991, *Elsevier Science Publishers B.V.*, Amsterdam, pp. 783-791.
E. J. Munson et al., "In Situ Solid-State NMR Study of Methanol-to-Gasoline Chemistry in Zeolite HSZSM-5", *Journal of Physical Chemistry*, 1992, vol. 96. No. 19, pp. 7740-7746.

(Continued)

*Primary Examiner*—Tam M Nguyen
(74) *Attorney, Agent, or Firm*—Dickstein Shapiro LLP

(57) ABSTRACT

Process for the separation of close boiling isomeric compounds comprising distilling a dilute solution of isomers in a high boiling compound in the presence of a solid adsorbent. Multi and/or monobranched as well as cyclic isomers are withdrawn at the top of the distillation column, while straight chain and/or mono branched isomers are retained within the solid adsorbent. The diluent solution of the high boiling compound is withdrawn from the bottom of the distillation column and recycled, where it may be combined with the feed isomer mixture or recycled straight to the top of the adsorption column.

9 Claims, 4 Drawing Sheets

OTHER PUBLICATIONS

J. Li et al., "Coke Formation During the Methanol Conversion to Olefins in Zeolites Studied by UV Raman Spectroscopy", *Microporous and Mesoporous Materials*, vol. 39, 2000, pp. 275-280.

C. Li et al., "Ultraviolet Raman Spectroscopy Characterization of Coke Formation in Zeolites", *Catalysis Today*, vol. 33, 1997, pp. 353-360.

S-J. Jong et al., "On the Regeneration of Coked H-ZSM-5 Catalysts", *Journal of Catalysis*, vol. 174, 1998, pp. 210-218, Article No. CA981971.

A.R. Pradhan et al., "EPR and NMR Studies of Coke Induced Selectivation Over H-ZSM-5 Zeolite During Ethylbenzene Disproportionation Reaction", *Journal of Catalysis*, vol. 184, 1999, pp. 29-38.

L-Y. Fang et al., "Enhanced *para*-Selectivity by Selective Coking During Toluene Disproportionation Over H-ZSM-5 Zeolite", Journal of Catalysis, vol. 185, 1999, pp. 33-42.

F. Bauer et al., "Reactivation of Coked H-ZSM-5 by Treatment with Hydrogen and Alkanes", *Journal of Catalysis*, vol. 164, 1996, pp. 146-151.

Gounaris et al. "Rational Design of Shape Selective Separation and Catalysis—I: Concepts and Analysis" *Chemical Engineering Science*, 61, 2006, pp. 7933-7948.

* cited by examiner

HYDROCARBON SEPARATION

FIELD OF THE INVENTION

The present invention relates to a process and apparatus for the separation of compounds having similar boiling temperatures. In particular, the invention relates to the separation of compounds of similar boiling temperatures in hydrocarbon isomerates, more particularly to the separation of mono and/or multibranched alkanes and cyclic alkanes from normal alkanes in $C_7$ isomerate mixtures such as the separation of n-$C_7$ from methylcyclohexane (MCH).

BACKGROUND OF THE INVENTION

The efficient removal of low-octane-number straight chain isomers, i.e. normal alkanes, from isomer mixtures is an important step in the generation of mixtures of high octane number for use in gasoline pools as well as for the efficiency of catalytic isomerisation processes. A number of processes have been disclosed dealing with this issue most of them related entirely to $C_5/C_6$ isomer blends.

U.S. Pat. No. 4,956,521 discloses the use of different adsorber beds with different specific zeolites for the removal of n-alkanes and mono-branched alkanes from $C_5/C_6$ isomers.

U.S. Pat. No. 6,069,289 describes a process for separating multimethylbranched alkanes, which are compounds of high octane number from the effluent of an isomerisation reactor by using a single adsorbent in a moving bed and two desorbents of different desorption capacities. The adsorbent may be silicalite, ferrierite, zeolite Beta, MAPO-31, SAPO-31, SAPO-11, and zeolite X and zeolite Y ion exchanged with cations.

U.S. Pat. No. 6,353,144 describes a process for separating isomers from a $C_5$-$C_8$ isomer mixture by injecting the isomer mixture into a chromatographic separation zone containing a zeolite adsorbent alternately with an eluent that enables the different adsorbed compounds of the isomer mixture to be desorbed.

U.S. Pat. No. 7,037,422 discloses a process for separating the high-octane-number compound naphta from an isomer mixture of $C_5$ and $C_6$ alkanes by contacting the isomer mixture with a CFI zeolite. Branched isomers of $C_5$ and $C_6$ alkanes are adsorbed and subsequently desorbed. In the zeolite, $C_5$ and $C_6$ alkanes are isomerised to the high octane number compounds methylbutane and dimethylbutane, and since methylbutane and dimethylbutane have a lower boiling point than, respectively, the other $C_5$-isomers and $C_6$-isomers, they are recovered by catalytic distillation in the same column.

SUMMARY OF THE INVENTION

We have now found that by diluting a hydrocarbon stream containing an isomerate mixture with a diluent solvent of higher boiling point, it is possible to separate close boiling isomeric hydrocarbons in a distillation column having an adsorbent arranged therein. In contrast with the processes of the prior art, we have surprisingly found that a distillation can be performed such that specific components can be retained in the column even if the boiling point is lower than the compounds distilling from the column. The other components boiling either higher or lower than the retained component(s) may be withdrawn as a distillate stream without carrying the diluent solvent.

Accordingly, we provide a process for the separation of isomers from an isomerate mixture comprising normal alkanes, mono-branched alkanes and multi-branched alkanes, the process comprising:
(a) passing said isomerate mixture to a distillation stage, said distillation stage comprising an adsorbent in an adsorption zone which is in contact with a diluent liquid solution having a boiling point which is higher than that of the isomerate mixture,
(b) withdrawing from said distillation stage a distillate stream containing mono-branched and/or multibranched alkanes and retaining in the adsorption stage at least said normal alkanes,
(c) withdrawing from said distillation stage a stream containing said diluent liquid solution and returning said stream to step (a).

Thus, the distillation in the presence of an adsorbent, particularly a solid zeolite adsorbent, enables in a simple manner the separation of mono-branched and/or multi-branched isomers from the isomerate mixture, since both distillation and adsorption are conducted in the same column. Accordingly, the process may be regarded as an "adsorptive isomer distillation" operating in batch mode.

The isomerate mixture may further comprise cyclic alkanes such as naphthenes and aromatic compounds such as benzene and toluene. The distillate stream will then also contain these compounds.

When said isomerate mixture (feed) contains cyclic alkanes such as naphthenes, these will be withdrawn in the distillate stream. This contrasts conventional distillation schemes, where such high boiling compounds are withdrawn from the distillation column bottom.

In step (b), by retaining in the adsorption stage at least said normal alkanes is meant that apart from normal alkanes, other compounds may be retained in the adsorbent, particularly mono-branched alkanes.

In a preferred embodiment of the invention step (a) comprises the steps of combining a first stream containing said isomerate mixture with a second stream of said diluent liquid solution having a boiling point which is higher than that of the isomerate mixture and passing the combined stream to said distillation stage. Thus, a diluent stream is withdrawn from the reactor and combined with the isomerate feed prior to entering the distillation unit containing the adsorbent.

It would be understood that the isomerate mixture and the diluent liquid solution may also be fed separately to the distillation column. Hence, the combination of a first stream containing the isomerate mixture with a second stream of a diluent liquid solution having a boiling point which is higher than that of the isomerate mixture may be conducted in a feeding region within the distillation column prior to the combined stream being exposed to the actual distillation stage or even in the immediate vicinity of the column, for instance in a mixing chamber in fluid communication with the distillation column.

In another embodiment in step (a) the diluent liquid solution is contacted with the first stream containing the isomerate mixture in counter-current mode in a distillation column comprising an adsorbent in an adsorption zone by withdrawing a stream of diluent from the bottom of the distillation column and returning said stream to the top of the column. In this manner the isomerate and diluent are combined within the distillation column as they pass counter-currently therein, thereby providing a much simpler construction of the column. There is no need for combining the streams before entering the column. Further, the introduction of the diluent at the top of the column secures full wetting of the column. The isomerate feedstock may advantageously be fed in undiluted form to a position between 5% to 50%, preferably about 10% to 30% from the column bottom. This enables a very good use of the zeolite adsorption capacity which, unexpectedly, approaches static room temperature adsorption conditions. In other words, despite the dynamic nature of the process, the adsorption capacity of the adsorbent approaches what is achieved under equilibrium conditions in a steady-state situation.

It would also be understood that instead of a single distillate stream, a number of distillate streams may be withdrawn from the column, and several adsorptive distillation columns with different adsorbents may be combined in series to improve the separation.

Although it is difficult to make a straightforward comparison with i.e. a chromatographic process such as that of U.S. Pat. No. 6,353,144, where a different feedstock is used and several streams are eluted from the adsorber, the present invention involves, as indicated above, a much better use of the adsorption capacity of the zeolite: the chromatographic method has an apparent capacity of 0.015 g feed/g adsorbent based on the described flow rate, time in service and the adsorbent mass in the individual columns, whereas the adsorptive distillation according to the present invention may treat about 0.2 g feed/g adsorbent before regeneration and still achieve a higher separation factor as defined below. In addition, the present invention enables the utilisation of the same column for 2-3 hrs, while the chromatographic method of U.S. Pat. No. 6,353,144 describes a charge time of 50 seconds/column between regenerations.

By the invention, the selectivity on the removal of normal alkanes increases dramatically. The selectivity is measured in terms of a separation factor (SF), which as used herein is defined by a weight ratio according to the following expression:

$$SF = \frac{([\text{Mono-and/or multi-branched alkanes}]/[\text{normal alkane}]s)_{product}}{([\text{Mono-and/or multi-branched alkanes}]/[\text{normal alkanes}])_{feed}}$$

For isomerate mixtures comprising methylcyclohexane (MCH) and n-heptane (n-$C_7$), average separation factors in the range 60-300 have been achieved over a 3 hrs period with maximum values as high as 2000. This represents a dramatic improvement with respect to prior art techniques, such as that described in U.S. Pat. No. 6,353,144, where the average separation factor between dibranched+ and n-alkanes (of a large isomer span) is at most 16 in periods of active adsorption of 50 sec depending on the chromatographic regeneration-elution procedure.

Without being bound by any theory it is believed that the presence of the diluent having a boiling point, which is higher than the isomerate mixture contributes to a highly efficient distribution of heat and mass within the distillation column, while the vapour pressure of the diluent still dominates. The temperature in the column being well above the boiling points of the $C_7$ isomerate components (approx. 80-105° C.) allows for establishing a vapour-liquid equilibrium in the column, where the adsorbates (primarily n-$C_7$) are believed to be adsorbed from the gas phase. In this manner the process works in a way as a very well controlled gas-phase adsorption, in which the gas phase is generated in the distillation column and the residence time is extended because of the liquid phase that also prevails within the column. The vapour-liquid equilibrium will further affect the adsorption-desorption equilibrium, which may have a benefit compared to an overall-gas phase process. At the same time the void volume is occupied due to the presence of the liquid diluent solution contributing to the performance of the column. Hence, by the invention we are able to minimize the void volume (adsorbent-free volume) of the column.

The hydrocarbon stream containing the isomerate mixture to be treated stems normally from an isomerisation process, where it is required that non-isomerised compounds which are separated are recycled to the process. By the invention it is possible to produce isomerate streams of high octane number (high RON/MON) and to reduce the volume of the recycle stream containing non-isomerised compounds, such as n-heptane, to the isomerisation process. Accordingly, the economy of the isomerisation process is significantly improved. Furthermore, the invention enables the removal of methylcyclohexane (MCH), which particularly in the case of treatment of recycle streams for isomerisation units is highly undesirable, since this compound is a coke precursor in said process.

The adsorbent is preferably a solid adsorbent, such as a zeolite. Accordingly, the adsorption of the distillation stage is conducted in an adsorption zone containing a zeolite selected from the group consisting of 5A, MCM-22, silicalite, ZSM-5 preferably with a Si/Al-ratio of between 25 and 400, ion exchanged HZSM-5 and mixtures thereof. Such zeolites have the required geometry, i.e. pore mouth and channel dimensions allowing optimal interaction between adsorbent and adsorbate. The zeolite geometry at pore mouth ("portal") level normally determines the selectivity between isomers in adsorption based processes. Not only should one determine the fit between molecule and zeolite by critical diameters and cross section diameters, but other molecular parameters should be involved as well to make the appropriate selection. A promising approach is by applying the recent method by Gounaris et al., *Chemical Engineering Science* 61 (2006) 7933-7948, where both the calculated molecular footprint and the strain on the molecule in very close molecule-zeolite portal fits will determine the penetration of the molecule especially in asymmetric zeolites. Especially in situations where mono-branched species has to be separated from multibranched the asymmetric aspect is of relevance. In general, cross section dimensions in the range of 5.0 to 5.5 Å for the minor axis and 5.5 to 6.0 Å for the major axis as described in the art are normally suitable for separation of n-alkanes and branched isomers. Other suitable adsorbents with pore geometry having selectivity for n-alkanes and/or mono-branched isomers may thus include MFI types like ZSM-11, ZSM-12, ZSM-23, ZSM-35, ZSM-48 and other alumino-silicates as well as ferrierite, MAPO-31, SAPO-5 SAPO-11, SAPO-31, EU-1, ion exchanged zeolite X and beta.

Upon use, the adsorption capacity in the adsorption zone of the distillation column decreases and therefore, a regeneration mode is provided to re-establish the adsorption capacity of the adsorbent by treatment with a desorbent that will specifically remove the adsorbate (e.g. normal alkanes) for further recovery and upgrading. Accordingly, the process comprises further desorbing the adsorbed alkanes from the adsorption zone by passing a desorbent stream through said adsorption zone and withdrawing a stream containing at least normal alkanes. Other components in this stream may include mono-branched alkanes, which are also trapped by the adsorbent. The group of components retained in the column and subsequently desorbed can be expanded depending on the adsorbent.

The desorbent may be any suitable compound that is capable of regenerating the adsorbent by removing the adsorbed alkanes from the adsorbent, such as hydrogen, nitrogen, isopentane, n-pentane, methane, n-butane, isobutane or mixtures thereof. Preferably, the desorbent is a stream of n-pentane or n-butane or a mixture of both compounds. The desorption (regeneration) may be performed according to any desorption technique known in the art. It may comprise desorption in the liquid state, i.e. at pressures above the saturation point of the desorbent, in the gas phase or in combination in which the pressure is regulated to operate in both liquid and gas phase. The operating pressure is preferably varied, while keeping the temperature of the distillation unit as constant as possible (isothermal). We have found that although the desorbent, for instance some n-pentane, may be present in the adsorbent upon reuse in a subsequent adsorption step, the performance of the adsorbent is unaffected during the adsorptive distillation, while significant amounts of n-pentane are distilled off.

In yet another embodiment of the process, prior to passing a desorbent stream through the adsorption zone, the diluent is removed from the column. This enables a better contact between desorbent and zeolite in the column during the desorption (regeneration) step.

According to the invention, the diluent liquid solution is preferably substantially free of isomers and is a solution of compounds selected from the group consisting of compounds comprising methyl, ethyl and propyl substituted benzenes and naphthenes boiling in the range from 135° C. to 200° C., in particular xylene, cumene, mesitylene, pseudocumene, durene, decalin and mixtures thereof.

A preferred diluent is mesitylene, since it has been found to give the highest efficiency particularly when treating $C_7$ isomerates. When operating with mesitylene, which has a boiling point of 165° C., the preferred process temperature of the desorption step is in the range of 140-160° C., that is 5° C. to 25° C. below the boiling point of the diluent depending on the process scheme and column feed point of isomerate and diluent. The relative lowering of the temperature during the distillation stage has been found to improve the distillate quality in terms of lowering the content of mesitylene in said distillate and also in terms of energy efficiency due to savings on the heat load. However, lowering the temperature too much may negatively affect the process. For instance, when using mesitylene as the diluent, isothermal column temperatures below 135° C. have shown no distillate production. Accordingly, the adsorption is preferably conducted at around the boiling point of the diluent liquid or the distillation temperature of the diluent-isomerate mixture, preferably at temperatures not more than 20° C. below the boiling point of the diluent liquid or the distillation temperature of the diluent-isomerate mixture.

In a further embodiment of the process the isomerate mixture comprising normal alkanes, mono-branched alkanes, multi-branched alkanes and cyclic alkanes (such as naphthenes) is a $C_7$-isomerate cut comprising n-heptane and methylcyclohexane (MCH). By the invention it is possible to treat hydrocarbon streams containing different isomerate cuts, like any mixtures of $C_5$ to $C_8$ alkanes, such as $C_5$ to $C_7$, $C_6$ to $C_7$, $C_6$ to $C_8$, or $C_8$, but more particularly intermediate $C_7$ cuts. The separation of isomers from such intermediate cuts of $C_7$-alkanes is particularly challenging, since this cut represents a particularly low octane group comprising mono-branched isomers which are significantly difficult to separate from the straight chain isomers (normal alkanes), while recovering the multi-branched isomers. The process according to the invention enables high selectivity in the separation of e.g. MCH (boiling at 101° C.) as distillate with respect to n-$C_7$ (boiling at 98° C.), which is in turn retained in the adsorbent. As described above, the MCH content is particular advantageous to control in isomerisation processes as recycling of this compound increases the deactivation of isomerisation catalysts due to coking.

The diluent liquid solution is preferably withdrawn from the distillation column at the bottom and may be returned (recycled) to the feed of the distillation column where it may be combined with the isomerate mixture. We have achieved diluent streams at the bottom of the column representing 96% to 99.5% of the diluent feed (i.e. we recover up to 99.5% of the diluent), depending on the extent of dilution imposed on the feed isomerate mixture as well as the column temperature. The column temperature will determine the distillate leaving the column, but also the content of mesitylene in the distillate. The higher the temperature the more mesitylene is found in the distillate, and also the separation in terms of mass of distillate is increased. The mesitylene content in the distillate effluent can be diminished to values as low as about 0.5 wt % by decreasing the temperature to no less than 145° C.

During the distillation, the highest boiling compounds of the isomerate mixture will be concentrated in the product being withdrawn at the top of the column. We have found that particularly high selectivities, i.e. high separation factors, are obtained when the weight percent of isomerate with respect to the diluent, preferably mesitylene, in the combined stream entering the distillation stage is 5% to 50%, preferably 10% to 30%, more preferably 15% to 25%, such as at about 20%.

The invention encompasses also the apparatus for carrying out the process. Accordingly, we provide a distillation column being heated along the entire or part of its length, comprising inlet means for the passage of separate streams of isomerate mixture and diluent liquid solution or inlet means for the passage of a combined stream of isomerate mixture and diluent liquid solution, outlet means for withdrawal of at least one distillate stream containing mono-branched and/or multibranched alkanes, outlet means for the withdrawal of a stream of a liquid solution containing said diluent, inlet means for the passage of a desorbent stream and outlet means for the withdrawal of a depressurized desorbent stream, wherein an adsorption zone packed with solid adsorbent material is arranged within said column.

The distillation column may further comprise a feeding region, where the mixing of isomerate mixture and diluent is conducted. This is particularly suitable when said isomerate mixture and diluent are fed separately to the distillation column.

DETAILED DESCRIPTION

Figure 1:
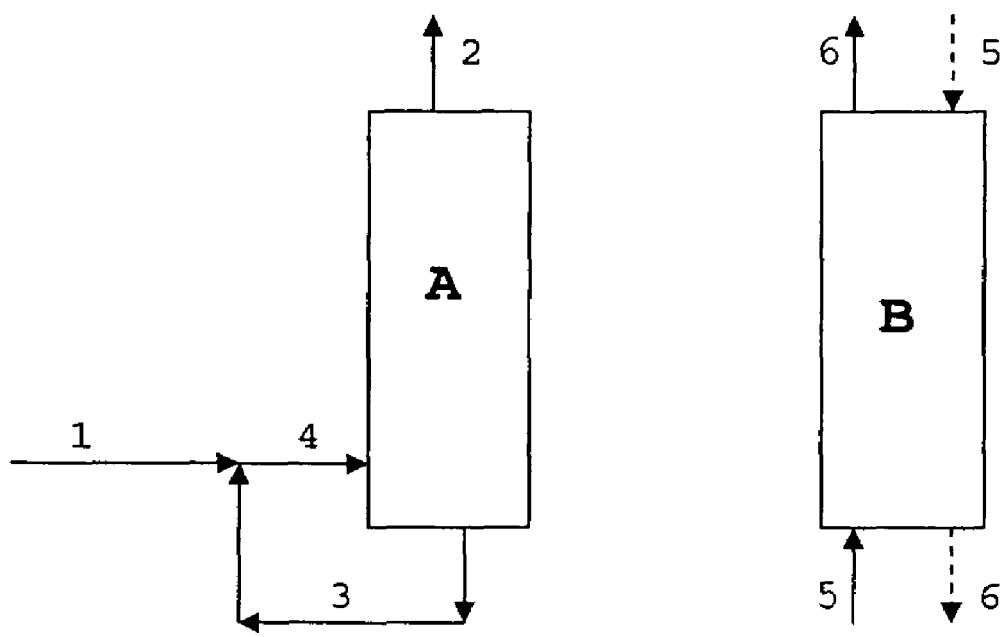
FIG. 1 shows a schematic of the distillation column in adsorption and desorption mode according to one embodiment of the invention in which the isomerate feed mixture and diluent are combined prior to entering the column.

FIG. 1 shows a schematic of the adsorption mode A and desorption mode B according to one embodiment of the process.

During adsorption and simultaneous distillation, an isomerate mixture 1 is combined with a diluent solution 3 to form a combined feed-diluent stream 4. The combined stream 4 enters the distillation column having disposed an adsorption zone therein. A distillate containing MCH, multi- and/or monobranched alkanes is withdrawn from the top as stream 2. By controlling the temperature of the column, the diluent can almost entirely be directed to the bottom and be withdrawn as effluent stream 3. In the adsorption zone of the column, n-alkanes are retained. The group of components retained can be expanded depending on the adsorbent. The effluent 3 of diluent liquid withdrawn at the bottom of the column is recycled and combined with the feed isomerate mixture 1. During the desorption step B, a stream 5 of a suitable desorbent such as pentane is injected. Pressure can be selected to perform this in the liquid or the gaseous state. The desorbent stream carrying the desorbed material (n-alkanes and/or mono-branched alkanes) will leave the top of the column as stream 6 in the co-current desorption mode. In counter-current desorption the desorbent is injected from the top 5' and leave with the desorbed components at the bottom of the column 6'.

Figure 2:
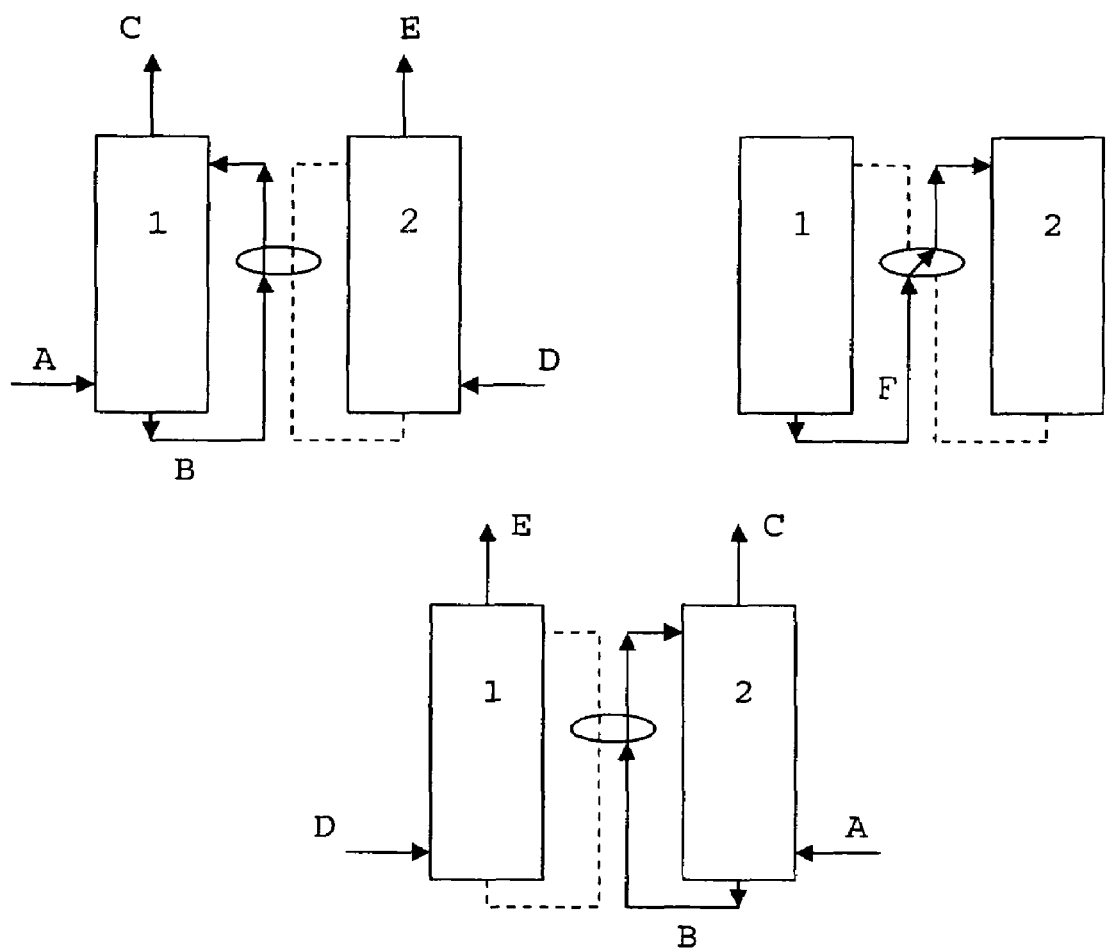
FIG. 2 shows a schematic of the distillation column in adsorption and desorption mode according to another embodiment of the invention in which the diluent is recycled directly to the top of the column.

In FIG. 2 the process runs with a direct recycle of the diluent from bottom to top. The figure shows a schematic description of the combination of two columns, where one column 1 operates in the adsorption mode and the other column 2 in the desorption mode. A is the feed point for isomerate, while B serves as the high boiling diluent solvent recycle that returns to the top of the column. The distillate stream C containing very low concentrations of the adsorbate (straight chain and/or mono-branched isomers) and low concentration of the high boiling diluent solvent added is withdrawn at the top. During the adsorptive distillation in column 1, column 2 is regenerated and the adsorbate is desorbed by pumping a stream D of desorbent, and by withdrawing a stream E of desorbent and adsorbate from the top of the column. The desorbent may be in the liquid or in the gaseous state. At the end of the adsorptive distillation step in column 1, the diluent stream F is pumped from the bottom of column 1 to the top of regenerated column 2 filling this column with the diluent and emptying column 1. This enables a better contact between desorbent and zeolite in column 1 during the desorption and regeneration step. The adsorptive distillation proceeds subsequently in column 2, while the desorption step is conducted in column 1.

Figure 3:
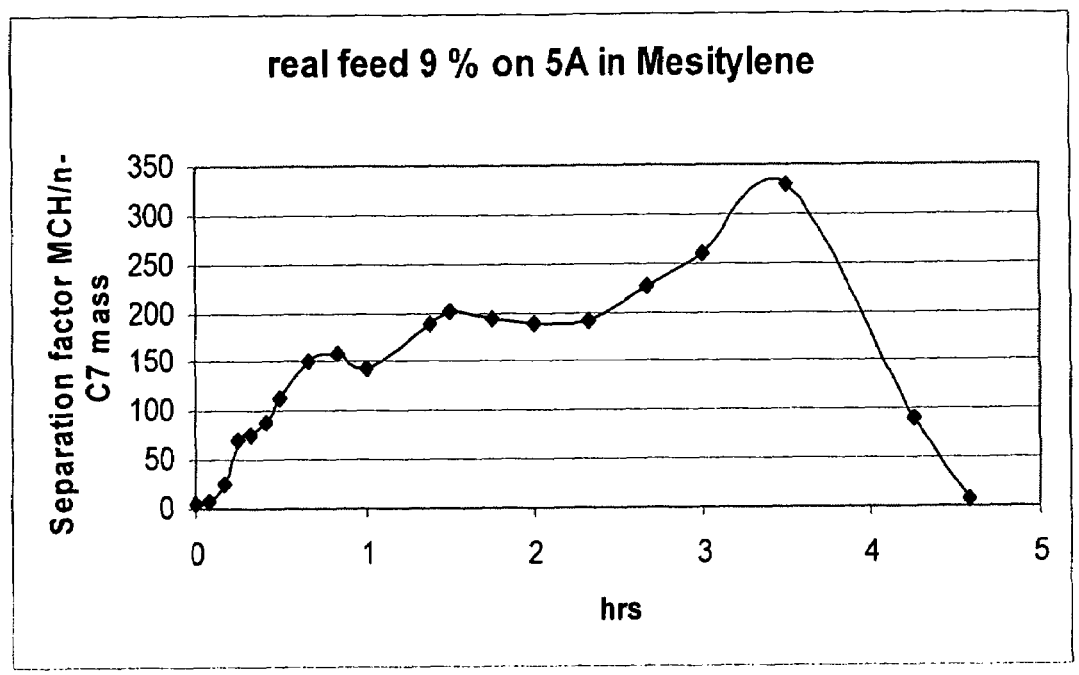
FIG. 3 shows a graph of the selectivity in terms of separation factor of MCH from an isomerate feed diluted with mesitylene.

FIG. 3 shows a graph of the selectivity in terms of separation factor of MCH from an isomerate mixture diluted 9 wt % with mesitylene over a zeolite 5A adsorbent. The C7 isomerate mixture represents a real feed having a number of mono and multi-branched as well as about 20 wt % n-heptane. It is seen that after a few hours of operation in the distillation column the selectivity for MCH in the distillate top product gradually increases reaching its maximum after about 3-4 hours with a separation factor above 300. A decline in separation factor at the end of the operation is observed as the adsorbent capacity is exhausted. The column was operated at a temperature close to the boiling point of mesitylene resulting in that the distillate had a significant content of mesitylene. As mentioned above, this can be avoided by operating the column at lower temperatures.

Figure 4:
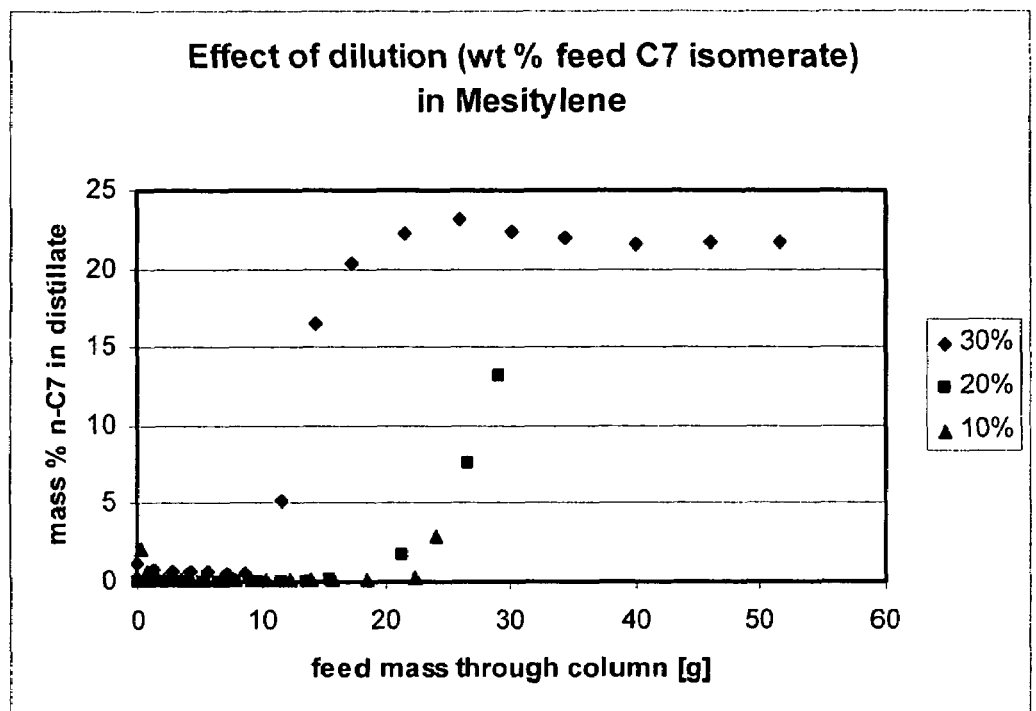
FIG. 4 is a graph showing the effect of dilution of the isomerate feed in mesitylene.

FIG. 4 shows the effect of dilution of the isomerate feed in mesitylene on distillate composition over a zeolite 5A adsorbent. The weight percent of isomerate in mesitylene is indicated in the graph. When the weight percent of isomerate in the liquid mesitylene solution in the combined stream entering the distillation stage is 10% the maximum value of the separation factor SF is about 250 increasing drastically to a maximum value of about 2000 when said weight percent is about 20% but decreasing sharply to a maximum value of about 40, when the weight percent of the isomerate in the diluent mixture increases to 30%.

EXAMPLES

Experiments were performed in a 90 cm fixed-bed zeolite column, which is used as a batch distillation unit heated along the entire length of the column. Two feeds were used: a real isomerate and a two-component mixture of n-heptane and methylcyclohexane (MCH). During the distillation, MCH being the highest boiling component of the two-component mixture is concentrated in the top product (boiling point MCH: 101° C., n-heptane: 98° C.). Mesitylene having a boiling point of 165° C. is used as diluent for the feed isomerate mixture. The dilution is in the range 10 wt % to 30 wt % feed in mesitylene. During the distillation, the diluent solvent is withdrawn from the bottom of the distillation unit and recycled. Zeolites extrudates of ZSM-5 and 5A were used as adsorbent materials in the distillation unit. Both adsorbents present a high selectivity for the n-alkanes, as revealed by average separation factors of up to 225 over several hours of continued distillation.

Example 1

Selective production of distillate stream of low heptane concentration from model isomerate system using pre-mixed feed. A column loaded with 432 g of 5A zeolite extrudate was heated to 165° C. The column had previously been used and regenerated by n-pentane flooding. The feed comprising a combined stream having n-heptane (0.83 wt %), methylcyclohexane (3.4 wt %) and mesitylene (95.8 wt %) was injected at a position 25% above the column bottom. As the process proceeded over 4.5 hrs, 824 g of feed was introduced resulting in three streams with the following average composition as shown in Table 1, the balance of the distillate being made up by n-pentane from the desorption.

TABLE 1

| wt % | Distillate | Bottom draw | Void |
|---|---|---|---|
| n-C$_7$ | 0.135 | 0.015 | 0.008 |
| methylcyclohexane (MCH) | 30.409 | 1.325 | 1.402 |
| Mesitylene | 54.610 | 98.438 | 98.566 |
| Separation factors for MCH/n-C$_7$ | 55 | 22 | 42 |

As observed the mesitylene bottom draw has a low content of n-heptane and can be recycled as diluent for the feed. The distillate contains a large fraction of MCH which during the run is much higher than the final combined distillate reported in Table 1. The inter-pellet void volume of the column is at the end of the run flushed and results again in a high diluent purity. The adsorbed species were desorbed with liquid n-pentane. The highest separation factor for MCH and n-C$_7$ measured during the process was 230, while the average over 4.5 hrs, as shown in the table (MCH/n-C$_7$) was 55. The initial first 30 minutes had an increasing trend in SF and a substantial n-pentane desorbent production. Although n-pentane was found in the distillate throughout the course of the test, this did not seem to severely affect the performance. However, we do know that much higher SF values are observed when operating a freshly loaded column, which has not been exposed to pentane. Due to the high column temperature in this test a substantial amount of mesitylene is bound to be found in the distillate. It is desirable and possible to control the column temperature at the top outlet to avoid mesitylene in the distillate. The present example runs with little mesitylene the first 1 hr, while the pentane content is high. Repeated experiments with different control of the top temperature shows that mesitylene content in the distillate effluent can be diminished to about 0.5 wt % by decreasing the temperature to no less than 145° C.

Example 2

Selective production of low heptane content distillate from real isomerate using pre-mixed feed. A mixture of 9% C$_7$ isomerate in mesitylene was charged to a column with pentane desorbed and regenerated 5A zeolite at a feed point 25% above the column bottom. The column temperature was isothermal and operated at 160° C. The compositions of feed and overall combined effluent streams are as given in Table 2.

TABLE 2

| Wt % | Feed | Distillate | Bottom draw | Void |
|---|---|---|---|---|
| n-C$_7$ | 1.76 | 0.05 | 0.05 | 0.30 |
| methylcyclohexane (MCH) | 1.10 | 2.02 | 0.31 | 0.43 |
| <n-C$_7$ | 5.37 | 10.47 | 0.63 | 1.30 |
| >n-C$_7$ (not incl. MCH) | 0.73 | 0.46 | 0.06 | 0.19 |
| n-pentane | 0 | 3.62 | 0.14 | 0.04 |
| mesitylene | 91.05 | 83.39 | 98.81 | 97.74 |

This experiment ran over a 4.5 hr period and hence represents a full loading of the zeolite with a capacity of 0.053 g n-heptane/g zeolite. Comparing this to a static room temperature capacity measurement of the zeolite of 0.050 g n-heptane/g zeolite the experiment shows that this process makes full use of the zeolite capacity despite of the use of much higher temperatures during the distillation. It is otherwise well known in the art that an increase in temperature greatly reduce the adsorption capacity of zeolites. The development of the separation factor between MCH and n-heptane is shown in FIG. 3.

Example 3

A column of freshly loaded zeolite 5A was fed 10% above the column bottom with a 6.5% C$_7$ isomerate in mesitylene solution at 165° C. The average n-heptane content after 3.5 hrs in service was 0.01 wt %. As only 11 g of heptane had passed the column due to the high dilution of the feed the capacity had not been exhausted and only approximately 40% of the capacity had been used. Due to the high temperature a substantial amount of mesitylene was also found in the distillate of this experiment.

Example 4

The above column was loaded with 426 g of zeolite 5A and the column was filled with mesitylene heated to 150° C. and the recycling from bottom to top was initiated at a low rate. At isothermal conditions the 100% feed isomerate was injected at a rate of approximately 50 g/hr for 3 hrs. The injection point was at 10% above the column bottom. The overall separation factor between MCH and n-C7 was approx 2100 over 3 hrs in service. Initial distillate (ca. 30 minutes) was more than 82% mono+multibranched. The first 10 minutes gave a multi-branched dominated distillate due to the temperature difference in boiling point between multi and mono-branched species. The feed and distillate composition is given in the Table 3 below. In this case the distillate made up 53% of the feed, as the desorption/regeneration step was initiated immediately after the adsorption mode with only a short post-distillation, hence a certain amount of the feed was never distilled from the column. The mass balance shows that 96% of the n-heptane was retained on the 5A zeolite. The active capacity for n-C7 was 0.07 g/g zeolite. The n-heptane in the distillate results from the last 30 minutes of the distillation.

TABLE 3

| | <n-C$_7$ | nC$_7$ | MCH | Mesitylene | >n-C$_7$ |
|---|---|---|---|---|---|
| Feed | 59.4 | 19.5 | 12.1 | 0 | 9.0 |
| Distillate | 81.9 | <0.02 | 15.1 | 0.1 | 2.5 |

What is claimed is:
1. Process for the separation of isomers from an isomerate mixture comprising normal alkanes, mono-branched alkanes and multi-branched alkanes, the process comprising:
  (a) passing said isomerate mixture to a distillation stage, said distillation stage comprising an adsorbent in an adsorption zone which is in contact with a diluent liquid solution having a boiling point which is higher than that of the isomerate mixture,
  (b) withdrawing from said distillation stage a distillate stream containing multi-branched and/or mono-branched alkanes and retaining in the adsorption stage at least said normal alkanes,
  (c) withdrawing from said distillation stage a stream containing said diluent liquid solution and returning said stream to step (a).
2. Process according to claim 1, wherein step (a) comprises the steps of combining a first stream containing said isomerate mixture with a second stream of said diluent liquid solution having a boiling point, which is higher than that of the isomerate mixture and passing the combined stream to said distillation stage.
3. Process according to claim 1, wherein in step (a) the diluent liquid solution is contacted with the first stream containing the isomerate mixture in counter-current mode in a distillation column comprising an adsorbent in an adsorption zone by withdrawing a stream of diluent from the bottom of the distillation column and returning said stream to the top of the column.
4. Process according to claim 1, wherein the adsorption stage of the distillation stage is conducted in an adsorption zone containing a zeolite selected from the group consisting of 5A, MCM-22, silicalite, ZSM-5, ion exchanged HZSM-5 and mixtures thereof.

5. Process according to claim 1, further comprising desorbing the adsorbed alkanes from the adsorption zone by passing a desorbent stream through said adsorption zone and withdrawing a stream containing at least normal alkanes.

6. Process according to claim 5, wherein the desorbent is hydrogen, nitrogen, isopentane, n-pentane, methane, n-butane, isobutane or mixtures thereof.

7. Process according to claim 1, wherein the diluent liquid solution is a solution of compounds selected from the group consisting of compounds comprising methyl, ethyl and propyl substituted benzenes and naphthenes boiling in the range from 135° C. to 200° C.

8. Process according to claim 1, where the isomerate mixture comprising normal alkanes mono-branched alkanes, multi-branched alkanes and cyclic alkanes is a $C_7$-isomerate cut comprising n-heptane and methylcyclohexane.

9. Process according to claim 2, wherein the weight percent of the isomerate with respect to the diluent in the combined stream entering the distillation stage is 5% to 50%.

* * * * *